(12) United States Patent
Butler et al.

(10) Patent No.: US 11,291,549 B2
(45) Date of Patent: Apr. 5, 2022

(54) CERAMIC ACETABULAR SHELL LINERS WITH AUGMENTS

(71) Applicant: DePuy Ireland Unlimited Company, Ringaskiddy (IE)

(72) Inventors: Lewis Butler, Leeds (GB); Ian J. Flatters, Sheffield (GB); Andrew W. Donn, Vancouver (CA); Alena M. Brandewie, Versailles, OH (US)

(73) Assignee: DePuy Ireland Unlimited Company, Ringaskiddy (IE)

(*) Notice: Subject to any disclaimer, the term of this patent is extended or adjusted under 35 U.S.C. 154(b) by 0 days.

(21) Appl. No.: 16/710,641

(22) Filed: Dec. 11, 2019

(65) Prior Publication Data
US 2021/0177606 A1    Jun. 17, 2021

(51) Int. Cl.
*A61F 2/34* (2006.01)
*A61F 2/30* (2006.01)
*A61F 2/32* (2006.01)

(52) U.S. Cl.
CPC ............ *A61F 2/34* (2013.01); *A61F 2/30734* (2013.01); *A61F 2002/30736* (2013.01); *A61F 2002/3241* (2013.01); *A61F 2002/3441* (2013.01); *A61F 2002/3483* (2013.01); *A61F 2002/3493* (2013.01); *A61F 2310/00023* (2013.01); *A61F 2310/00179* (2013.01)

(58) Field of Classification Search
CPC ..................... A61F 2/34; A61F 2/30734; A61F 2002/30736; A61F 2002/3241; A61F 2002/3425; A61F 2002/3443; A61F 2002/3493; A61F 2310/00179
See application file for complete search history.

(56) References Cited

U.S. PATENT DOCUMENTS

| | | | |
|---|---|---|---|
| 3,707,006 A | 12/1972 | Bokros et al. |
| 3,801,989 A | 4/1974 | McKee |
| 3,818,514 A | 6/1974 | Clark |
| 3,829,904 A | 8/1974 | Ling et al. |
| 4,714,477 A | 12/1987 | Fichera et al. |
| 4,993,410 A | 2/1991 | Kimsey |
| 5,133,763 A | 7/1992 | Mullers |
| 5,133,765 A | 7/1992 | Cuilleron |
| 5,147,366 A | 9/1992 | Arroyo et al. |

(Continued)

FOREIGN PATENT DOCUMENTS

| | | |
|---|---|---|
| CN | 2580920 Y | 10/2003 |
| CN | 101883540 A | 11/2010 |

(Continued)

*Primary Examiner* — Brian A Dukert
(74) *Attorney, Agent, or Firm* — Barnes & Thornburg LLP

(57) ABSTRACT

An acetabular prosthesis for use in a hip arthroplasty surgical procedure is disclosed. The acetabular prosthesis includes a ceramic acetabular shell liner component configured to be secured to an acetabular shell component. The acetabular prosthesis also includes a metal ring affixed to and encircling the ceramic acetabular shell liner component. The acetabular prosthesis also includes an augment molded to and distally extending from the metal ring. The augment is shaped to modify a range of motion of a femoral prosthetic component when the femoral prosthetic component is fitted into the ceramic acetabular shell liner component. Other embodiments are also disclosed.

20 Claims, 17 Drawing Sheets

(56) References Cited

U.S. PATENT DOCUMENTS

| | | |
|---|---|---|
| 5,156,626 A | 10/1992 | Broderick et al. |
| 5,405,394 A | 4/1995 | Davidson |
| 5,425,779 A | 6/1995 | Schlosser et al. |
| 5,458,649 A | 10/1995 | Spotorno et al. |
| 5,549,691 A | 8/1996 | Harwin |
| 5,569,263 A | 10/1996 | Hein |
| 5,674,225 A | 10/1997 | Mueller |
| 5,735,905 A | 4/1998 | Parr |
| 5,865,850 A | 2/1999 | Matthews |
| 5,885,295 A | 3/1999 | McDaniel et al. |
| 5,888,211 A | 3/1999 | Sanders |
| 6,110,179 A | 8/2000 | Flivik et al. |
| 6,284,002 B1 | 9/2001 | Sotereanos |
| 6,344,060 B1 | 2/2002 | Schmotzer et al. |
| 6,488,713 B1 | 12/2002 | Hershberger |
| 6,585,771 B1 | 7/2003 | Buttermilch et al. |
| 7,179,297 B2 | 2/2007 | McLean |
| 7,192,449 B1 | 3/2007 | McQueen et al. |
| 7,819,925 B2 | 10/2010 | King et al. |
| 7,833,452 B2 | 11/2010 | Muratoglu et al. |
| 8,293,811 B2 | 10/2012 | Muratoglu et al. |
| 8,461,225 B2 | 6/2013 | Muratoglu et al. |
| 8,679,187 B2 * | 3/2014 | Allen .................. A61F 2/4637 623/22.24 |
| 8,840,676 B2 | 9/2014 | Belew et al. |
| 8,858,645 B2 | 10/2014 | Grostefon et al. |
| 8,888,859 B2 | 11/2014 | Muratoglu et al. |
| 9,168,683 B2 | 10/2015 | Muratoglu et al. |
| 9,615,927 B2 | 4/2017 | Huff et al. |
| 9,724,201 B2 | 8/2017 | Grostefon et al. |
| 2001/0037156 A1 | 11/2001 | Burstein et al. |
| 2002/0052661 A1 | 5/2002 | Spotorno et al. |
| 2002/0193882 A1 | 12/2002 | Koller |
| 2003/0144742 A1 | 7/2003 | King et al. |
| 2004/0115172 A1 | 6/2004 | Bianchi et al. |
| 2004/0117029 A1 | 6/2004 | Lewis et al. |
| 2004/0199257 A1 | 10/2004 | Dooney |
| 2005/0143828 A1 | 6/2005 | Collins et al. |
| 2005/0146070 A1 | 7/2005 | Muratoglu et al. |
| 2007/0100464 A1 | 5/2007 | Meulink |
| 2007/0118227 A1 | 5/2007 | King et al. |
| 2007/0250175 A1 | 10/2007 | Meridew et al. |
| 2008/0172130 A1 * | 7/2008 | Macara .................. A61F 2/34 623/22.21 |
| 2008/0215142 A1 | 9/2008 | Muratoglu et al. |
| 2009/0036993 A1 | 2/2009 | Metzger |
| 2010/0082101 A1 | 4/2010 | Muratoglu et al. |
| 2010/0131073 A1 | 5/2010 | Meridew et al. |
| 2010/0241239 A1 | 9/2010 | Smith |
| 2011/0247229 A1 | 10/2011 | Anapliotis et al. |
| 2012/0089235 A1 | 4/2012 | Conway et al. |
| 2012/0185059 A1 | 7/2012 | Vankoski et al. |
| 2012/0319332 A1 | 12/2012 | Mcminn |
| 2013/0060344 A1 | 3/2013 | Pierce |
| 2013/0204389 A1 | 8/2013 | Kumar et al. |
| 2013/0245775 A1 | 9/2013 | Metcalfe |
| 2013/0325139 A1 | 12/2013 | Steiner et al. |
| 2016/0074167 A1 | 3/2016 | Vautrin |

FOREIGN PATENT DOCUMENTS

| | | |
|---|---|---|
| CN | 102458311 A | 5/2012 |
| DE | 10335442 A1 | 2/2005 |
| DE | 102008030260 A1 | 12/2009 |
| EP | 0207873 A1 | 1/1987 |
| EP | 0342014 A1 | 11/1989 |
| EP | 0663194 A1 | 7/1995 |
| EP | 0807426 A2 | 11/1997 |
| EP | 1293179 A1 | 3/2003 |
| EP | 1359950 A1 | 11/2003 |
| EP | 1223895 B1 | 12/2006 |
| EP | 1091705 B1 | 8/2007 |
| EP | 1825834 A1 | 8/2007 |
| EP | 2198808 A1 | 6/2010 |
| EP | 1841686 B1 | 2/2012 |
| EP | 2574310 A2 | 4/2013 |
| FR | 1481424 A | 5/1967 |
| FR | 2105998 A5 | 4/1972 |
| GB | 1485295 A | 9/1977 |
| GB | 2042897 A | 10/1980 |
| GB | 2152385 A | 8/1985 |
| JP | 11155890 A | 6/1999 |
| JP | 3172112 B2 | 6/2001 |
| JP | 2002345858 A | 12/2002 |
| JP | 2003175061 A | 6/2003 |
| JP | 4051950 B2 | 2/2008 |
| JP | 6007386 B2 | 10/2016 |
| RU | 2309706 C2 | 11/2007 |
| WO | 9522944 A1 | 8/1995 |
| WO | 03049649 A1 | 6/2003 |
| WO | 2004069096 A2 | 8/2004 |
| WO | 2008117056 A1 | 10/2008 |
| WO | 2009106867 A1 | 9/2009 |
| WO | 2010129880 A2 | 11/2010 |
| WO | 2012035294 A2 | 3/2012 |
| WO | 2016200735 A1 | 12/2016 |
| WO | 2017003570 A1 | 1/2017 |
| WO | 2017053183 A1 | 3/2017 |

* cited by examiner

CERAMIC ACETABULAR SHELL LINERS WITH AUGMENTS

TECHNICAL FIELD

The present disclosure relates generally to orthopaedic prosthetic components and, more particularly, to acetabular prosthetic components.

BACKGROUND

Joint arthroplasty is a surgical procedure in which a patient's natural joint is replaced by a prosthetic joint. In a hip arthroplasty procedure, at least a portion of a patient's hip ball and socket joint is replaced with one or more corresponding prosthetic components. For example, the socket portion of the joint, known as the acetabulum, may be replaced with one or more acetabular prosthetic components (e.g., an acetabular shell that fits within the acetabulum and a liner that fits within the shell to act as a bearing surface). Similarly, the ball portion of the joint, known as the femoral head, may be replaced with a femoral head prosthetic component. While many acetabular shell liners are semi-hemispherical in shape (e.g., generally shaped as a hemi-sphere but not necessarily defining a perfect hemisphere), some patients may obtain enhanced results when the geometry of the liner is augmented to be over-hemispherical (e.g., defining more than a hemisphere).

SUMMARY

In one aspect, the present disclosure includes an acetabular prosthesis for use in a hip arthroplasty surgical procedure. The acetabular prosthesis includes a ceramic acetabular shell liner component configured to be secured to an acetabular shell component. The acetabular prosthesis also includes a metal ring affixed to and encircling the ceramic acetabular shell liner component. The acetabular prosthesis also includes an augment molded to and distally extending from the metal ring. The augment is shaped to modify a range of motion of a femoral prosthetic component when the femoral prosthetic component is fitted into the ceramic acetabular shell liner component.

In some embodiments, the ceramic acetabular shell liner component may be semi-hemispherical in shape and the augment may cause the acetabular prosthesis to be over-hemispherical in shape. The ceramic acetabular shell liner component may include an outer wall that is shaped to define a channel around a perimeter of the outer wall and the metal ring may be secured within the channel. Additionally, in some embodiments, the metal ring includes titanium. In some embodiments, the metal ring may be at least partially coated with a polymeric material. The metal ring may additionally or alternatively include a set of keys that extend from the ring in the distal direction and the augment may be molded over the set of keys. In some embodiments, the augment may include a polymeric material.

In another aspect, the present disclosure includes an acetabular prosthesis for use in a hip arthroplasty surgical procedure. The acetabular prosthesis includes a ceramic acetabular shell liner component configured to be secured to an acetabular shell component. The acetabular prosthesis also includes an augment, separate from the ceramic acetabular shell liner component. The augment includes a set of tabs that extend in a proximal direction and are shaped to secure the augment to the ceramic acetabular shell liner component when the ceramic acetabular shell liner component is fitted into the acetabular shell component.

In some embodiments, each tab of the set of tabs is shaped to fit into a corresponding slot defined in a rim of the acetabular shell component. Each tab of the set of tabs may be tapered and configured to interface with a corresponding taper of the ceramic acetabular shell liner component. The taper of the set of tabs and the taper of the ceramic acetabular shell liner component may form an interference lock. In some embodiments, the augment may include a channel that is shaped to straddle at least a portion of a rim of the acetabular shell component. The augment may include a polymeric material. In some embodiments, the ceramic acetabular shell liner component is semi-hemispherical in shape and the augment causes the acetabular prosthesis to be over-hemispherical in shape. The augment may be shaped to modify a range of motion of a femoral prosthetic component when the femoral prosthetic component is fitted into the ceramic acetabular shell liner component.

In yet another aspect, the present disclosure includes an acetabular prosthesis for use in a hip arthroplasty surgical procedure. The acetabular prosthesis includes an acetabular shell liner component configured to be secured to an acetabular shell component. The acetabular shell liner component includes a ceramic inner bearing layer having a ceramic semi-hemispherical body and an integral ceramic augment extending distally from the semi-hemispherical body. The acetabular shell liner component also includes a metallic outer reinforcement layer affixed to an outer wall of the ceramic semi-hemispherical body and an outer wall of the integral ceramic augment of the ceramic inner bearing layer.

The metallic outer support layer of the acetabular prosthesis may be coated with a polymeric material. In some embodiments, the metallic outer support layer may be shaped to be received into the acetabular shell component. The acetabular shell liner component may include a rim having a proximal portion that, when the acetabular shell liner component is in the acetabular shell component, is substantially co-planar with a rim of the acetabular shell component. The augment may define a distal portion of the rim of the acetabular shell liner component that is a first distance from the rim of the acetabular shell component and the proximal portion of the rim is a second distance from the rim of the acetabular shell component. The first distance may be greater than the second distance. In at least some embodiments, the augment may be shaped to modify a range of motion of a femoral prosthetic component when the femoral prosthetic component is fitted into the acetabular shell liner component.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements. The detailed description particularly refers to the accompanying figures in which.

DETAILED DESCRIPTION OF THE DRAWINGS

Figure 1:
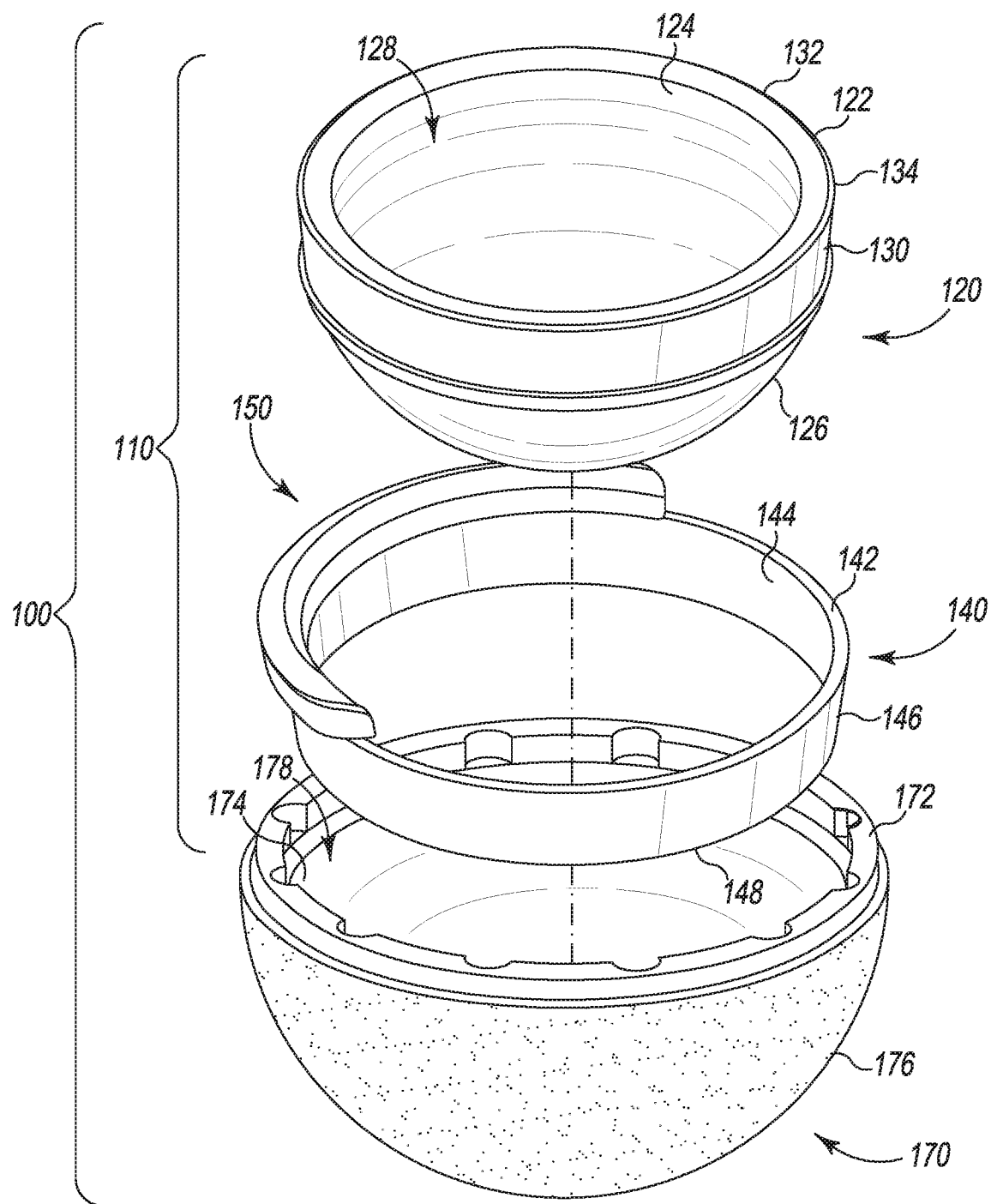
FIG. 1 is an exploded perspective view of an embodiment of a modular acetabular prosthesis having a ceramic acetabular shell liner, a metal ring that affixes to the ceramic acetabular shell liner and provides an augment, and an acetabular shell to receive the ceramic liner and metal ring.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, an illustrative modular acetabular prosthesis 100 includes an acetabular shell liner assembly 110 and an acetabular shell component 170 (also referred to herein as an acetabular shell). In use (e.g., during a hip arthroplasty procedure), the acetabular shell liner assembly 110 is configured to be received into the acetabular shell component 170. In the illustrative embodiment, the acetabular shell liner assembly 110 includes a ceramic acetabular shell liner component 120 (also referred to herein as an acetabular shell liner) and a metal ring 140 configured to affix to and encircle the ceramic acetabular shell liner component 120. As discussed in more detail herein, the ring 140 supports (e.g., provides a foundation for, provides reinforcement to, is affixed to, etc.) an augment 150 that, when the ring 140 is affixed to the ceramic acetabular shell liner 120, augments the geometry of the ceramic acetabular shell liner 120. That is, the ceramic acetabular shell liner 120 is generally semi-hemispherical in shape (e.g., generally hemispherical in shape but not necessarily defining a perfect hemisphere). However, when the ceramic acetabular shell liner 120 is combined with the augment 150, which extends in a distal direction away from a rim 122 of the acetabular shell liner 120, the resulting geometry of the acetabular shell liner assembly 110 is generally over-hemispherical in shape (e.g., defining more than half of a sphere). The augmented geometry may provide enhanced results for some patients, such as improving joint stability through a greater range of flexion than other geometries. Furthermore, by supporting the augment 150 on the metal ring 140, the ceramic acetabular shell liner 120 may be manufactured in a single standardized shape while metal rings 140 having different augments 150 (e.g., of differing geometries and/or materials) may be separately manufactured and affixed to the standardized ceramic acetabular shell liner 120 during an assembly process to obtain a variety of different acetabular shell liner assemblies 110 having different properties (e.g., geometries, materials, etc.).

In the illustrative embodiment, the ceramic acetabular shell liner 120 includes a rim 122 having an inner edge 132 and an outer edge 134. A generally hemi-spherical concave inner wall 124 extends inwardly from the rim 122 (e.g., from the inner edge 132) in a proximal direction to define a cavity 128. The cavity 128 is sized and shaped to receive a femoral head (e.g., a femoral head component of a prosthesis or a natural femoral head). As such, the inner wall 124, in operation, acts as a bearing surface for a femoral head. Opposite the inner wall 124, the ceramic acetabular shell liner 120 includes a generally semi-hemispherical convex outer wall 126. The outer wall 126 includes a channel 130, which may be embodied as a recessed portion that extends around a perimeter of the outer wall 126. The channel 130 is sized and shaped to securely engage with the metal ring 140, which, during assembly, is slid into or otherwise positioned within the channel 130.

In the illustrative embodiment, the metal ring 140 is annular in shape (e.g., to encircle the outer wall 126 of the ceramic liner 120), and includes a distal rim 142, a proximal rim 148, an inner wall 144 that extends between the distal rim 142 and the proximal rim 148 along an inner perimeter of the ring 140, and an outer wall 146 that extends between the distal rim 142 and the proximal rim 148 along an outer perimeter of the ring 140. The metal of the ring 140 in the illustrative embodiment includes titanium. However, in other embodiments, the metal may include additional or alternative metals (e.g., steel). In some embodiments, the metal ring 140 may be coated with a polymeric material (e.g., polyetheretherketone (PEEK), carbon-fiber-reinforced polyetheretherketone (CFR PEEK), low friction ultra-high-molecular-weight polyethylene (UHMWPE), etc.), to provide enhancements to the prosthesis 100 (e.g., inhibiting corrosion, reducing a potential for damage to the femoral head during an instability event, etc.). The augment 150, which may be molded onto the metal ring 140 as described in more detail herein, is illustratively made of a polymeric material such as UHMWPE.

The acetabular shell component 170 is somewhat similar in shape to the ceramic liner 120, in that the acetabular shell component 170 is generally semi-hemispherical. In the illustrative embodiment, the acetabular shell component 170 includes a rim 172, a concave inner wall 174 that extends inwardly from the rim 172 in a proximal direction to define a cavity 178 (e.g., to receive the acetabular shell liner assembly 110), and a convex outer wall 176 that extends from the rim 172 in the proximal direction, opposite the inner wall 174. In the illustrative embodiment, the acetabular shell component 170 is made of a metal (e.g., steel). Further, the outer wall 176 of the acetabular shell component 170 has a porous surface to enhance the engagement of the acetabular shell component 170 to an inner surface of a patient's surgically prepared acetabulum (e.g., by promoting bone growth into porous surface). In some embodiments, the porous surface may be a porous coating, such Porocoat® Porous Coating which is commercially available from DePuy Synthes Products, Inc. of Warsaw, Ind.

Figure 2:
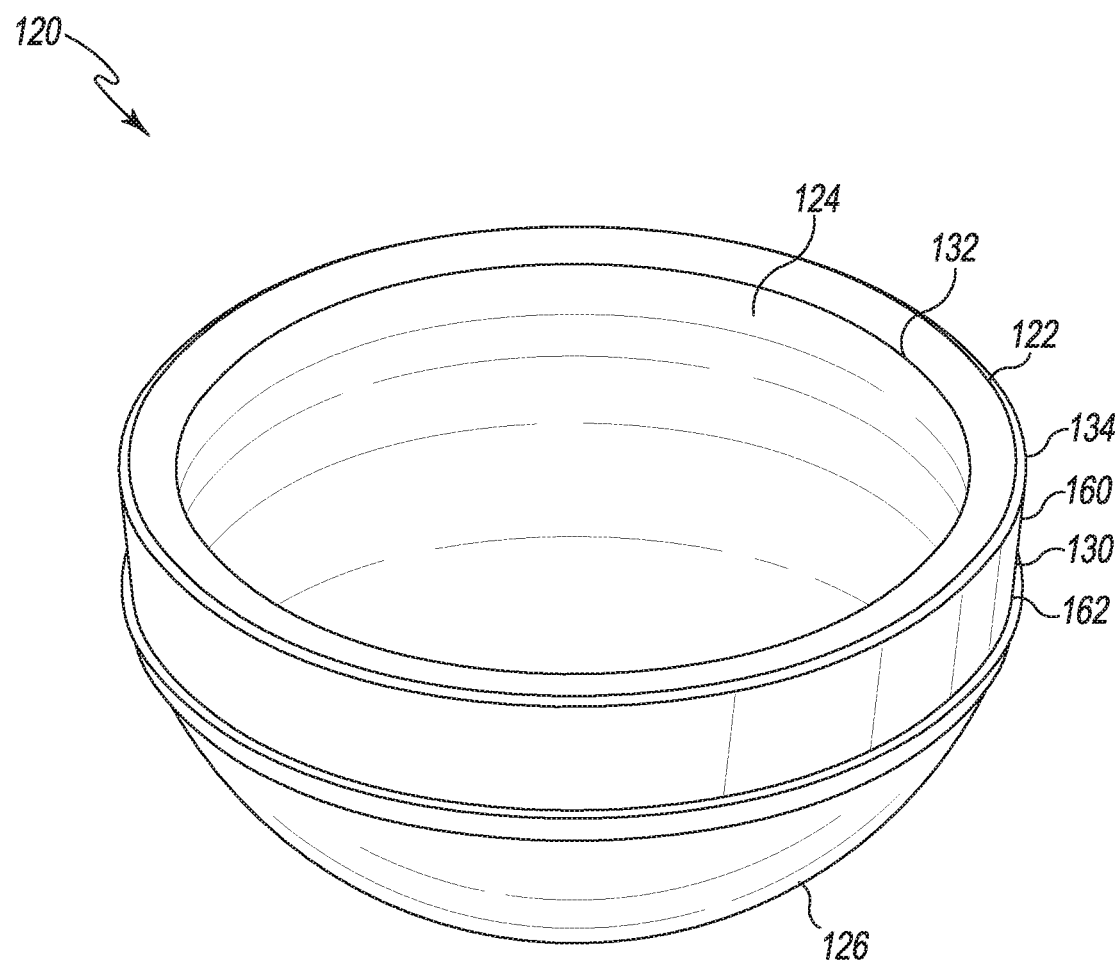
FIG. 2 is a perspective view of the ceramic acetabular shell liner of FIG. 1.

Referring now to FIG. 2, in one stage of a manufacturing process, the ceramic acetabular shell liner 120 is produced. As discussed above, in the illustrative embodiment, the ceramic acetabular shell liner 120 includes the channel 130 to accommodate and securely engage with the metal ring 140. The channel 130 extends between a distal edge 160 and a proximal edge 162 around the outer wall 126 of the ceramic acetabular shell liner 120. In the illustrative embodiment, the recess that defines the channel 130 in the outer wall 126 does not affect the shape of the inner wall 124, which is generally semi-hemispherical and smooth to provide a continuous bearing surface for a femoral head.

Figure 3:
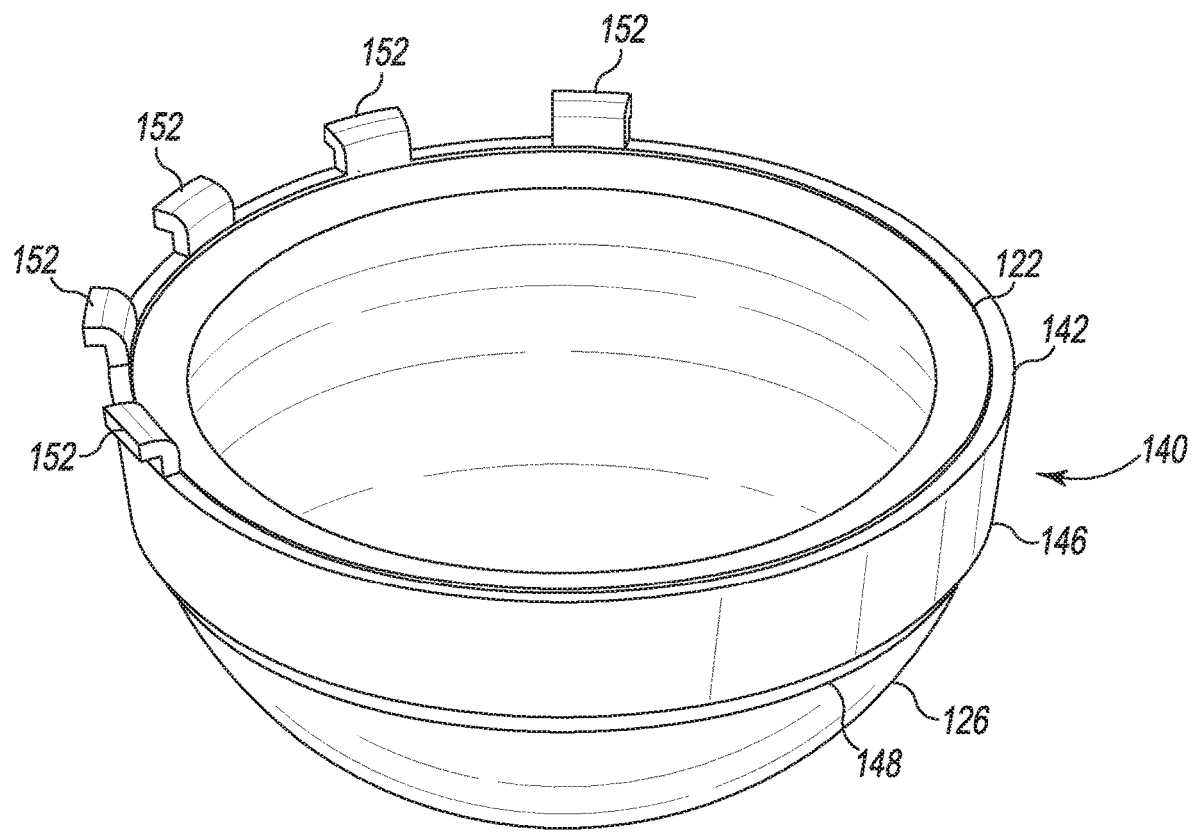
FIG. 3 is a perspective view of the ceramic acetabular shell liner of FIG. 1, with the metal ring affixed to the liner and a set of keys extending from the metal ring to support an augment.

Referring now to FIG. 3, in a subsequent stage of the manufacturing process, the metal ring 140 is press fit into the channel 130, such that the distal edge 160 and proximal edge 162 of the channel 130 resist movement of the ring 140 in a distal or proximal direction. Furthermore, in the illustrative embodiment, the fit between the ring 140 and the outer wall 126 of the liner 120 is sufficiently tight to resist other movement (e.g., rotation) of the ring 140 relative to the liner 120. In some embodiments, to reduce the possibility of the ring 140 sliding distally past the channel 130, the ring 140 and the channel 130 may have a tapered geometry in which the proximal rim 148 of the ring 140 is smaller in diameter than the distal rim 142 of the ring 140 and, likewise, the proximal edge 162 of the channel 130 is smaller in diameter than the distal edge 160 of the channel 130. As shown, in at least some embodiments, the ring 140 includes a set of keys 152 or protrusions, each of which extends generally in a distal direction away from the distal rim 142 of the ring 140 and acts as a foundation, skeleton, or inner support structure onto which the augment 150 may be molded. The keys 152, in addition to extending distally, may also curve outwards from the ring 140, as shown in FIG. 3. In other embodiments, the keys 152 may have a different shape. The material from which keys 152 are made may be metal (e.g., the metal used in the ring 140, such as titanium), a polymeric material (e.g., UHMWPE), or other material.

Figure 4:
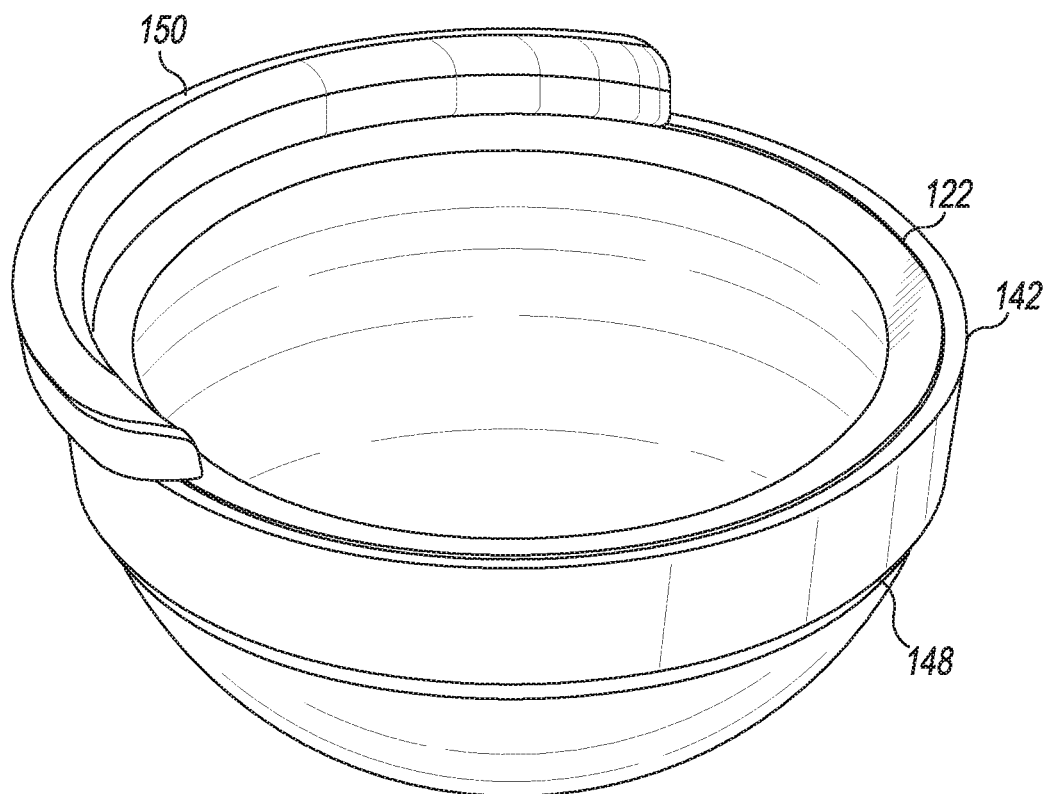
FIG. 4 is a perspective view of the ceramic acetabular shell liner of FIG. 1, with the metal ring affixed to the liner, and the augment molded over the set of keys.

Referring now to FIG. 4, in a subsequent stage of the manufacturing process, the augment 150 is affixed to the ring 140. In the illustrative embodiment, the augment 150 is molded over the keys 152 shown in FIG. 2. In other embodiments, the augment 150 may be affixed to the ring 140 by another method (e.g., through a mechanical connection, such as by inserting the keys 152 into corresponding slots in the augment that are shaped to provide an interference lock with the keys 152). As described above, and as will be appreciated from the process shown in FIGS. 3-5, different augments having different geometries may be formed on the ring 140, without affecting the shape or manufacture of the ceramic acetabular shell liner 120 itself.

Figure 5:
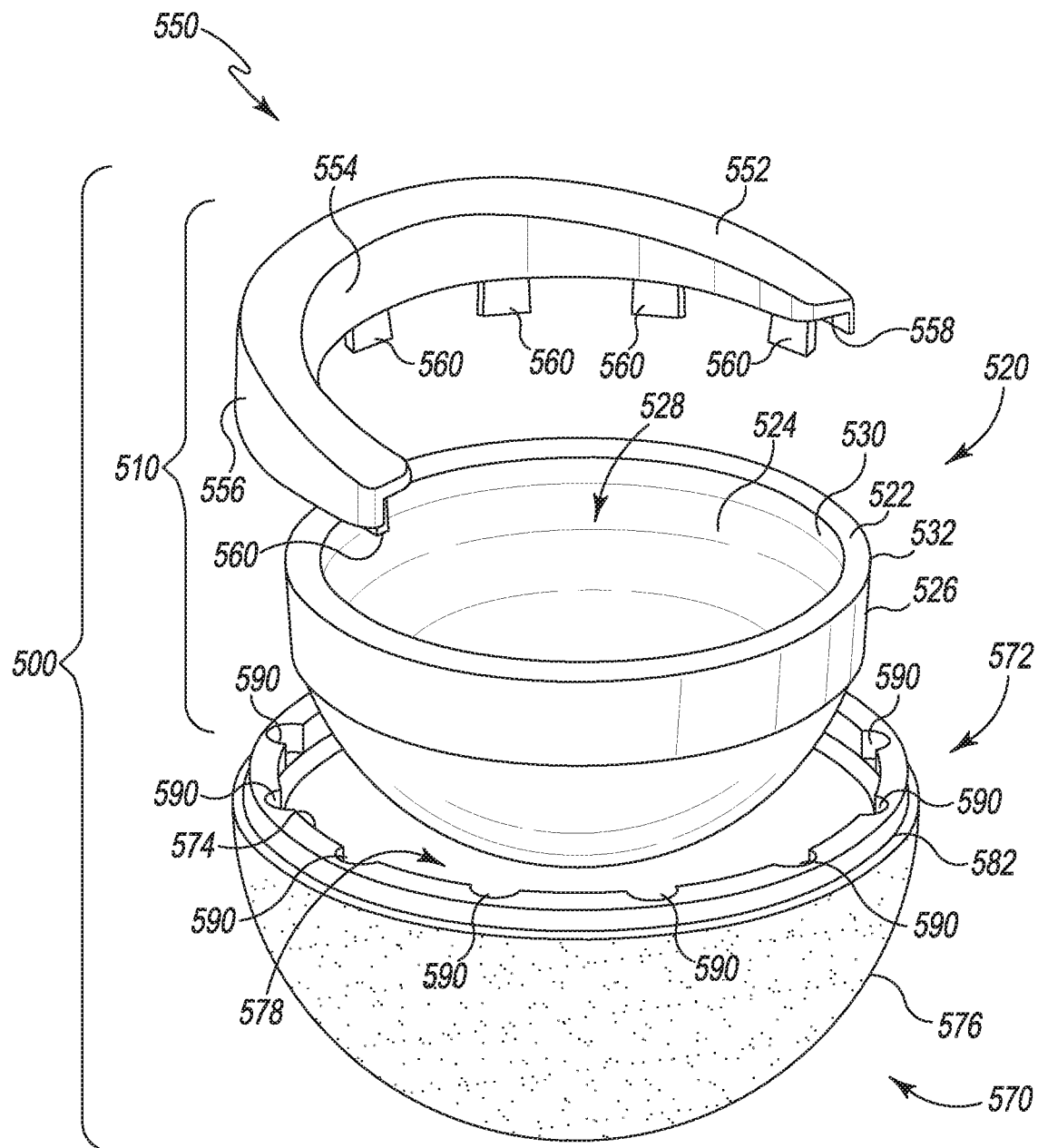
FIG. 5 is an exploded perspective view of an alternative embodiment of a modular acetabular prosthesis having a ceramic acetabular shell liner, an augment having a set of tabs that secure the augment to the liner, and an acetabular shell.

Referring now to FIG. 5, another embodiment of a modular acetabular prosthesis 500 includes an acetabular shell liner assembly 510 and an acetabular shell component 570 (also referred to herein as an acetabular shell). The acetabular shell liner assembly 510 includes a ceramic acetabular shell liner component 520 (also referred to herein as an acetabular shell liner) and an augment 550. The ceramic acetabular shell liner component 520 is generally semi-hemispherical in shape and is similar to the acetabular shell liner component 120. In the illustrative embodiment, the ceramic acetabular shell liner component 520 includes a rim 522 with an inner edge 530 and an outer edge 532, a concave inner wall 524 that extends inwardly in a proximal direction from the rim 522 (e.g., from the inner edge 530 of the rim 522) and a convex outer wall 526, opposite the inner wall 524, that extends in the proximal direction from the rim 522 (e.g., from the outer edge 532 of the rim 522). The concave inner wall 524 defines a cavity 528 shaped to receive a femoral head, and, as such, the inner wall 524 acts as a bearing surface for the femoral head.

The augment 550, in some respects, is similar to the augment 150, in that the augment 550 modifies the geometry of the acetabular shell liner 520 such that the combined acetabular shell liner assembly 510 is over-hemispherical in shape (e.g., defines more than a hemisphere but less than a total sphere). As such, like the augment 150, the augment 550 may provide enhancements for some patients, such as increased joint stability. However, unlike the augment 150, the augment 550 is not molded onto or otherwise permanently affixed to a metal ring (e.g., the metal ring 140) that fits around an acetabular shell liner. Rather, the augment 550, in the illustrative embodiment, is a separately manufactured component that "snaps" (e.g., press fits) into engagement with the ceramic acetabular shell liner 520 and the acetabular shell component 570 using a set of tabs 560 or protrusions that extend in a proximal direction and interface with corresponding components of the acetabular shell liner 520 and acetabular shell component 570, as described in more detail herein.

The acetabular shell component 570 is similar in many respects to the acetabular shell component 170, in that the acetabular shell component 570 includes a rim 572, a concave inner wall 574 that extends inwardly in a proximal direction to define a cavity 578, and a convex outer wall 576 that extends in the proximal direction from the rim 572, opposite the inner wall 574. Like the outer wall 176, the outer wall 576 may have a porous surface (e.g., a porous coating). Further, in the illustrative embodiment, the rim 572 includes an inner portion 580 and an outer portion 582. As shown, the inner portion 580 extends slightly further in a distal direction than the outer portion 582 of the rim 572. Further, the inner portion 580 of the rim 572 includes slots 590 or recesses spaced around the perimeter of the inner portion 580. The slots 590 function to resist rotation of a component (e.g., the augment 550) having corresponding parts (e.g., the tabs 560) that fit into one or more of the slots 590.

The augment 550, in the illustrative embodiment, is generally curved (e.g., from a plan view) and shaped to fit over a portion (e.g., less than the entire perimeter) of the rim 522 of the ceramic acetabular shell liner 520 and a corresponding portion of the rim 572 of the acetabular shell component 570. Illustratively, the augment 550 includes a rim 552 from which an inner wall 554 extends in a proximal direction and an outer wall 556, opposite the inner wall 554, extends in the proximal direction. The augment 550 defines a channel 558 or recess that extends along a curved path between the outer wall 556 and the tabs 560. The channel 558 is sized and shaped to straddle (e.g., fit around) the inner portion 580 of the rim 572 of the acetabular shell 570 (e.g., to resist lateral movement of the augment 550 relative to the acetabular shell 570). To further resist undesired movement of the augment 550, the tabs 560 are sized and shaped to fit within corresponding slots 590 or recesses in the rim 572 of the acetabular shell 570 and to be locked in place (e.g., by an interference lock formed by a taper interface between each tab 560 and the outer edge 532 of the rim 522 of the ceramic liner 520). The fit of the tabs 560 is described in greater detail with reference to FIG. 7 below.

Figure 6:
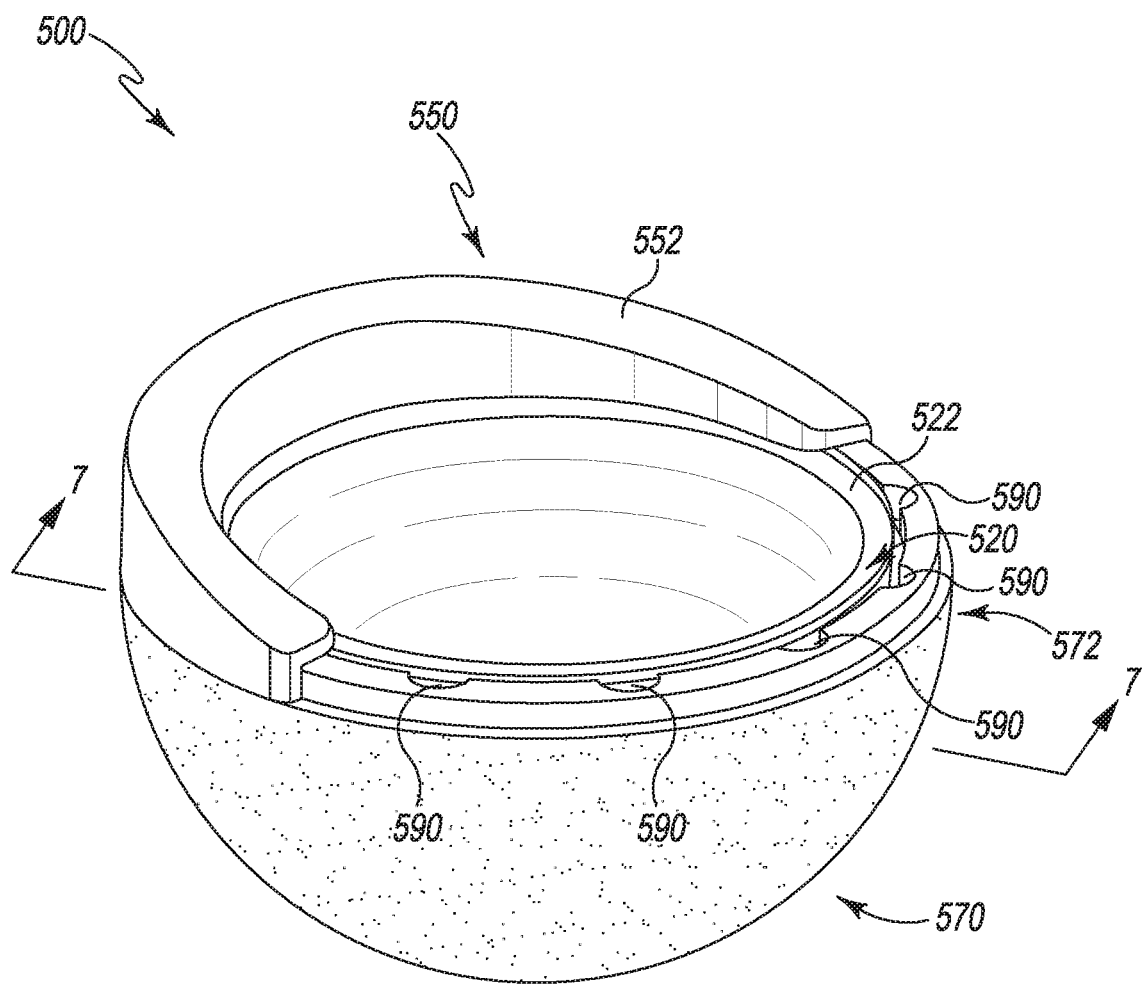
FIG. 6 is a perspective view of the modular acetabular prosthesis of FIG. 5 in which the acetabular shell liner, the augment, and acetabular shell are secured together.
Figure 7:
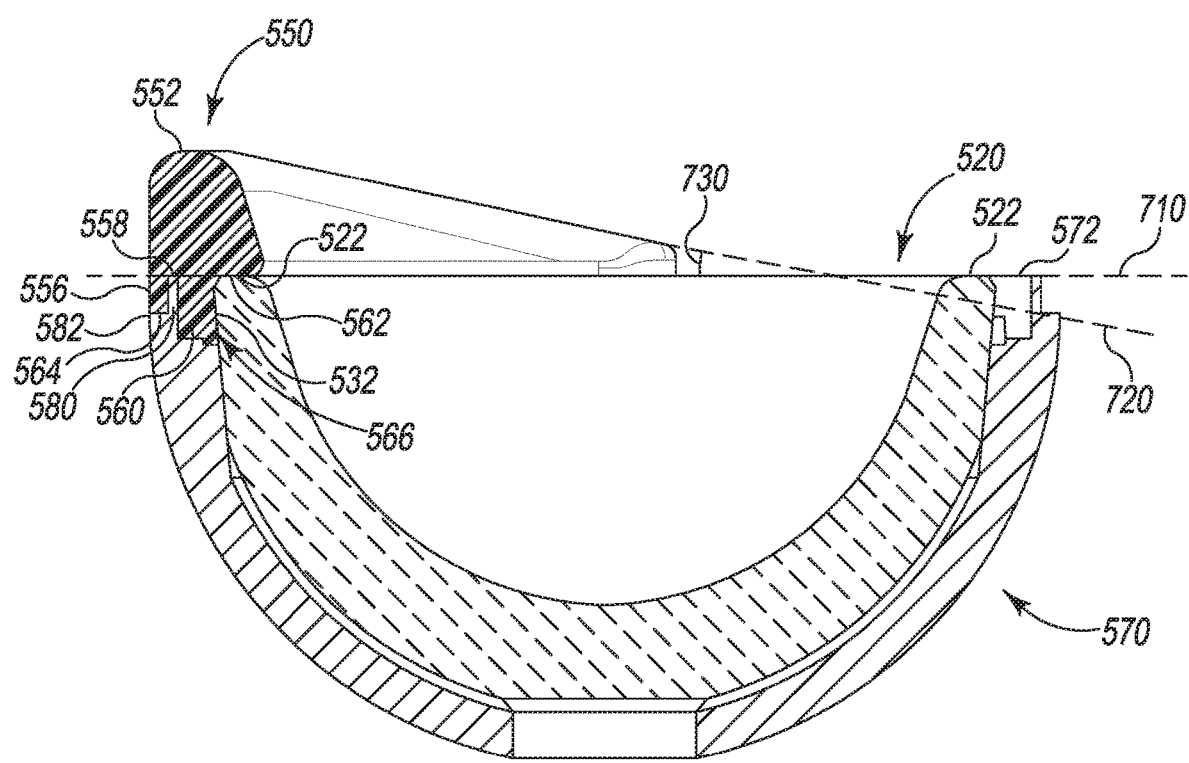
FIG. 7 is a cross-sectional elevation view of the modular acetabular prosthesis of FIG. 5, taken along line 7-7 of FIG. 6.

Referring now to FIG. 6, the modular acetabular prosthesis 500 is shown in its assembled form. As shown, the ceramic acetabular shell liner 520 fits within the acetabular shell 570 and the augment 550 fits over the rims 522, 572, providing the otherwise generally semi-hemispherical prosthesis an over-hemispherical geometry (e.g., to improve the stability of the resulting joint). Referring to FIG. 7, it can be seen that the rims 522, 572 are substantially coplanar (e.g., defining an imaginary plane 710) while the augment 550 defines an imaginary plane 720 at a non-orthogonal angle 730 (e.g., 15 degrees) to the imaginary plane 710. Focusing now on the fit between the augment 550, the acetabular shell liner 520, and the acetabular shell 570, it can be seen that each tab 560 of the augment 550 is interposed or squeezed between the ceramic liner 520 and the acetabular shell 570 near their rims 522, 572 (e.g., between the outer edge 532 of the rim 522 and the inner portion 580 of the rim 572). In the illustrative embodiment, the outer edge 532 is tapered outwards (e.g., increasing in diameter moving from a proximal portion of the outer edge 532 to a distal portion of the outer edge 532) and the tab 560 has a corresponding taper, such that a taper interface 566 is formed between the tab 560 and the outer edge 532 of the rim 522 of the liner 520. Additionally, as can be seen in FIG. 7, the channel 558 straddles the inner portion 580 of the rim 572 of the acetabular shell 570. Further, the augment 550 has a flat contact portion 562 that rests upon the rim 522 of the ceramic liner 520 and another flat contact portion 564 that rests upon the outer portion 582 of the rim 572 of the acetabular shell 570. The flat contact portions 562, 564 may operate to shield stress on the tabs 560 during flexion of the prosthetic joint.

Figure 8:
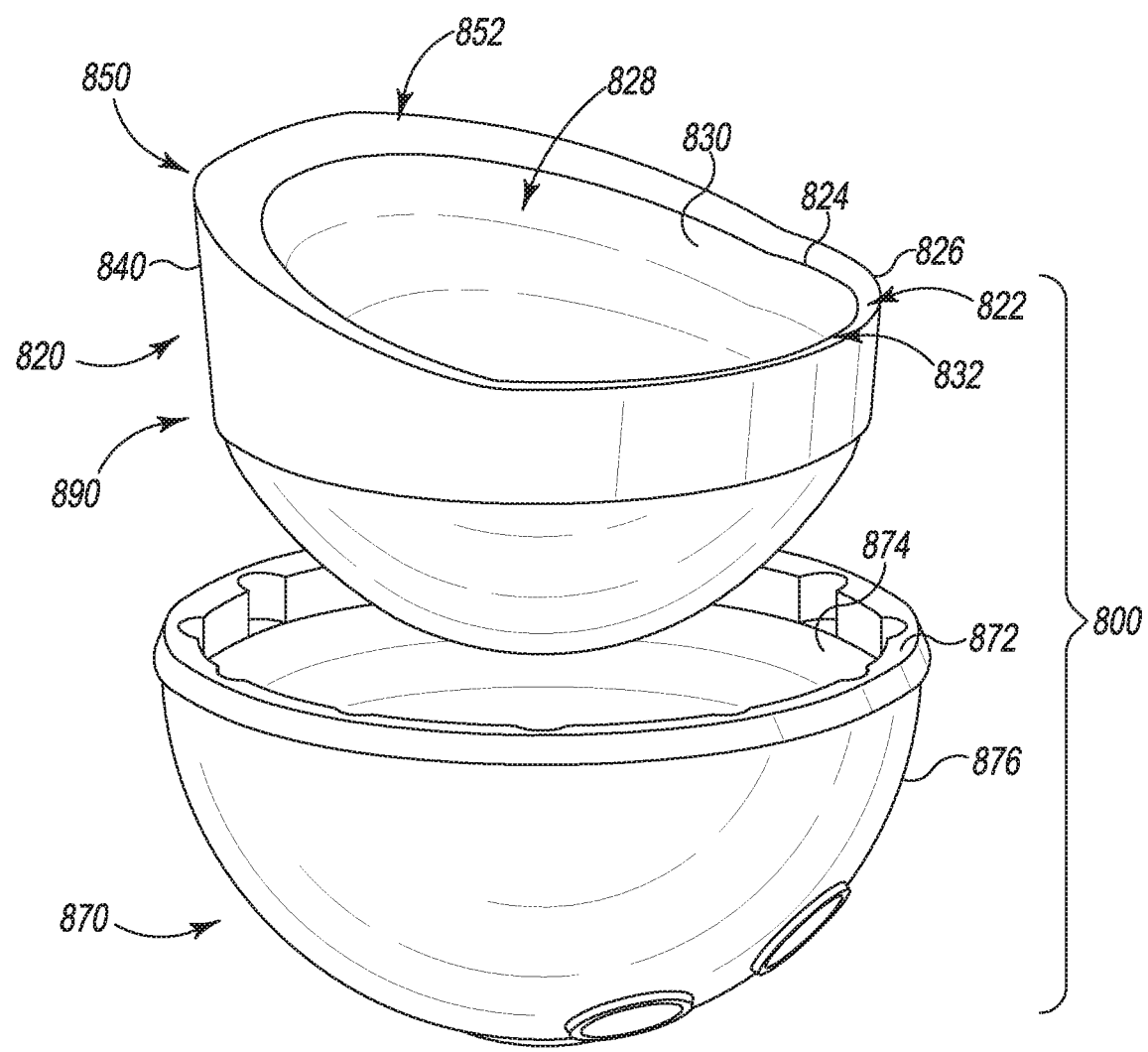
FIG. 8 is an exploded perspective view of an alternative embodiment of a modular acetabular prosthesis having a hybrid augmented acetabular shell liner with a ceramic inner bearing layer, a metal outer support layer, and an integrated augment, and an acetabular shell.

Referring now to FIG. 8, in another embodiment of a modular acetabular prosthesis 800, a hybrid augmented acetabular shell liner component 820 (also referred to herein as a hybrid augment acetabular shell liner) is shaped to fit into a corresponding acetabular shell component 870 (also referred to herein as an acetabular shell). The acetabular shell 870 is similar to acetabular shell 570 in that the acetabular shell 870 includes a rim 872, a concave inner wall 874 extending inwardly in a proximal direction to define a cavity, and a convex outer wall 876 extending from the rim 872 in the proximal direction. Referring back to the hybrid augmented acetabular shell liner 820, unlike the liners 120 and 520, the liner 820 is manufactured to have an integrated augment 850 (e.g., augment 850 is not a separate piece that is fitted or affixed to the liner 820). Further, the liner 820 is a hybrid liner in that the liner 820 includes two layers of different material. That is, in the illustrative embodiment, the liner 820 includes an inner bearing layer 830, which is concave and made of ceramic, and an outer reinforcement layer 840, which is convex and made of metal (e.g., titanium). The outer reinforcement layer 840 is generally coextensive with the inner bearing layer 830, providing a relatively strong backing to the ceramic even in sections (e.g., the integrated augment 850) that are not reinforced by the acetabular shell 870 when the prosthesis 800 is assembled. In some embodiments, the metal of the outer reinforcement layer 840 may be coated with a polymeric material.

As can be seen in FIG. 8, the liner 820 includes a rim 822 with an inner edge 824 and an outer edge 826 opposite the inner edge 824. The inner bearing layer 830 extends inwardly in a proximal direction from the inner edge 824 of the rim 822 and defines a cavity 828 shaped to receive a femoral head. The outer reinforcement layer 840 extends in a proximal direction from an outer edge 826 of the rim 822 and is shaped to be received into the acetabular shell 870. The liner 820 has a generally semi-hemispherical body 890 formed by generally semi-hemispherical portions of the inner bearing layer 830 and the outer reinforcement layer 840. The augment 850, which extends distally from the semi-hemispherical body 890, gives the liner 820 an over-hemispherical shape. As stated above, and as shown in FIG. 8, the augment 850 is integral to the acetabular shell liner 820 and, in the illustrative embodiment, the rim 822 is continuous between the body 890 and the augment 850. As such, the rim 822 has a proximal portion 832 (e.g., a rim of the body 890) and a distal portion 852 (e.g., a rim of the augment 850).

Figure 9:
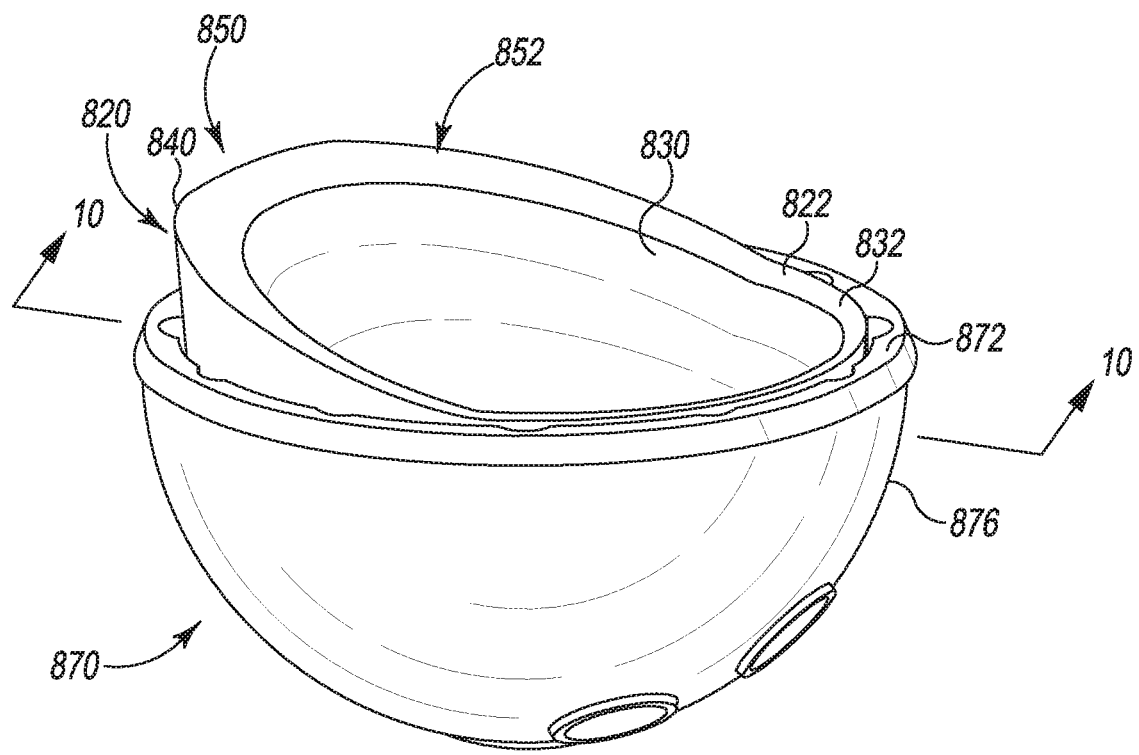
FIG. 9 is a perspective view of the modular acetabular prosthesis of FIG. 8 in which the hybrid augmented acetabular shell is secured in the acetabular shell.

Referring now to FIG. 9, the acetabular prosthesis 800 is shown in its assembled form. As can be seen, the hybrid liner 820 fits within (e.g., press fits and locks within) the acetabular shell 870 and the augment 850 extends distally therefrom, providing an over-hemispherical shape to the prosthesis 800. While the acetabular shell 870 provides reinforcement to the body 890 of the liner 820 when the liner 820 is secured therein, the ceramic augment 850, which extends out of the acetabular shell 870, is reinforced by the metal outer reinforcement layer 840.

Figure 10:
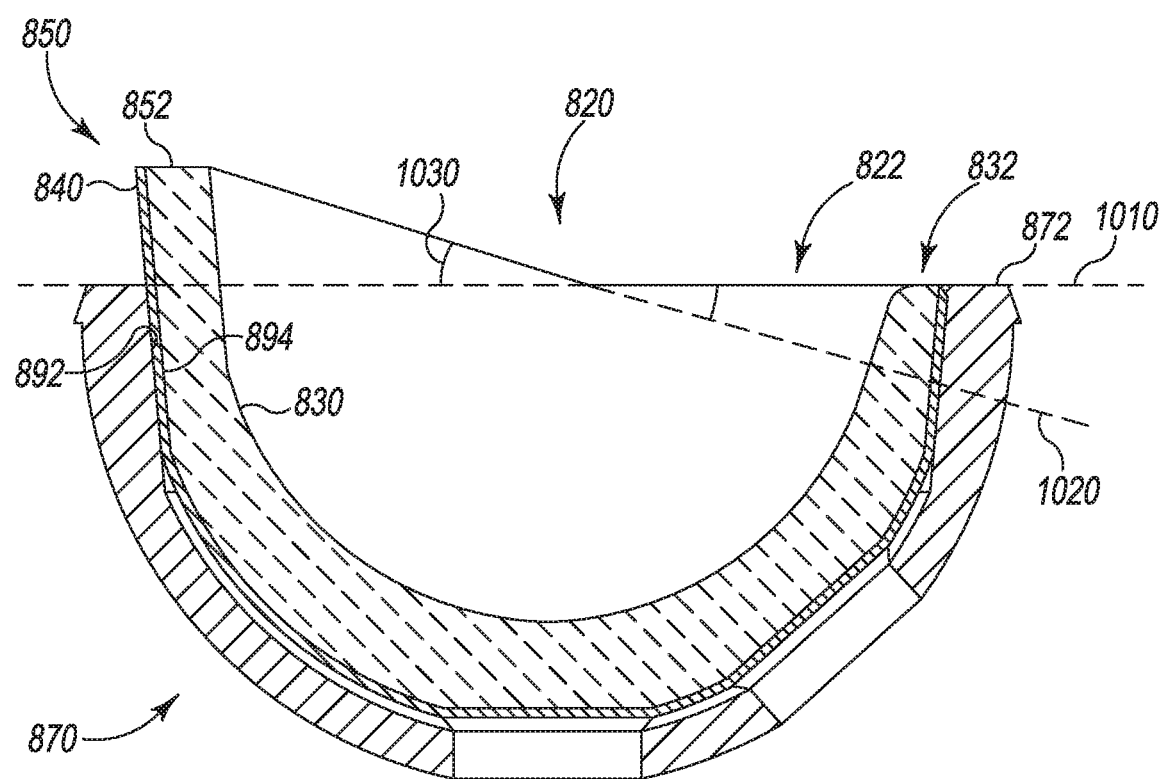
FIG. 10 is a cross-sectional elevation view of the modular acetabular prosthesis of FIG. 8 taken along line 10-10 of FIG. 9.

Referring now to FIG. 10 it can be seen that an inner wall 892 of the metal outer reinforcement layer 840 is affixed to an outer wall 894 of the ceramic inner bearing layer 896 (e.g., during a manufacturing process). Further, the over-hemispherical shape of the hybrid acetabular shell liner 820 can be seen. The rim 872 and the proximal portion 832 of the rim 822 are generally co-planar, forming an imaginary plane 1010 and the augment 850 forms an imaginary plane 1020 that is at a non-orthogonal angle 1030 (e.g., 15 degrees) to the imaginary plane 1010. The resulting geometry is an over-hemispherical shape (e.g., defining more than a hemisphere but less than a total sphere) that may provide enhanced joint stability for some patients.

Figure 11:
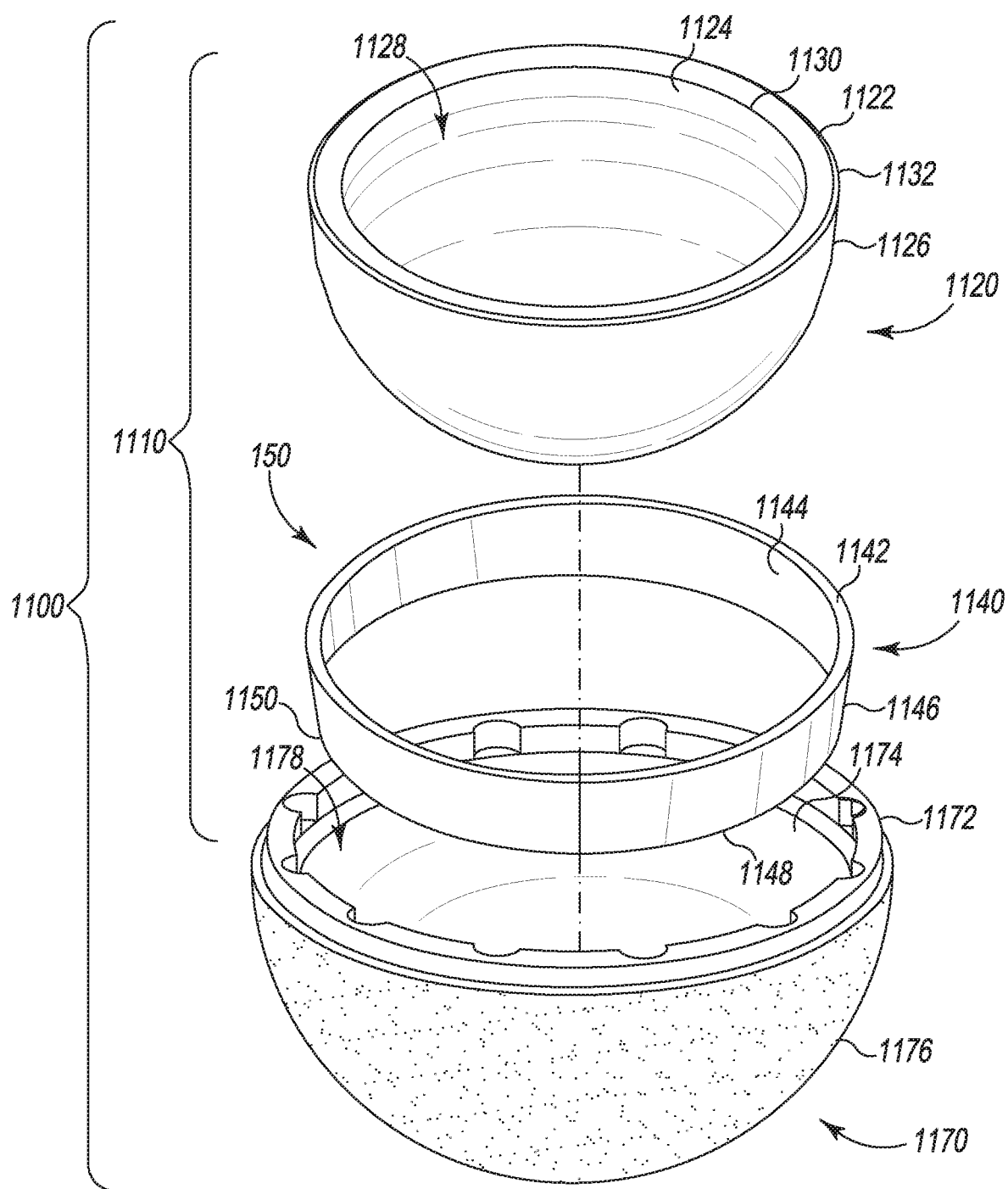
FIG. 11 is an exploded perspective view of another embodiment of a modular acetabular prosthesis having a ceramic acetabular shell liner, an acetabular shell, and a metal ring that aligns the acetabular shell liner with the acetabular shell during assembly.

Referring now to FIG. 11, another embodiment of a modular acetabular prosthesis 1100 includes a modular acetabular shell liner assembly 1110 and an acetabular shell component 1170 (also referred to herein as an acetabular shell). The acetabular shell component 1170 is similar to the acetabular shells 170, 570, 870 and is generally semi-hemispherical in shape, with a rim 1172, a concave inner wall 1174 that extends inwardly in a proximal direction to define a cavity (e.g., to receive the acetabular liner assembly 1110), and a convex outer wall 1176 which extends in the proximal direction from the rim 1172 and is shaped to fit within a surgically prepared acetabulum. The acetabular shell, in the illustrative embodiment, is made of metal and, like the acetabular shells 170, 570, 870, may have a porous surface (e.g., a porous coating) on the outer wall 1176 (e.g., to enhance the engagement of the acetabular shell 1170 with an inner surface of the acetabulum).

The acetabular shell liner assembly 1110, in the illustrative embodiment, includes a ceramic acetabular shell liner component 1120 (also referred to herein as the ceramic acetabular shell liner) and a metal ring 1140 that affixes to (e.g., press fits onto) and encircles the ceramic acetabular shell liner 1120. The ceramic acetabular shell liner 1120 is generally semi-hemispherical in shape, with a rim 1122 having an inner edge 1130 and an outer edge 1132, a concave inner wall 1124 that extends inwardly in a proximal direction from the inner edge 1130 to defined a cavity 1128 shaped to receive a femoral head, and a convex outer wall 1126 that extends in the proximal direction opposite the inner wall 1124 and is shaped to be received into the cavity 1178.

The metal ring 1140, which may be made of titanium or another metal, functions as a shield to absorb impacts when the liner assembly is being fitted into the acetabular shell component 1170 during a hip arthroplasty procedure. The metal ring 1140 also operates to align the liner assembly 1110 into the acetabular shell component 1170 during insertion. That is, in the illustrative embodiment, the metal ring 1140, which is annular in shape and has an inner wall 1144 and an outer wall 1146 that both extend between a distal rim 1142 and a proximal rim 1148, has a lead-in surface 1150 at the proximal rim 1148 that is rounded and guides or centers the acetabular shell liner assembly 1110 into the cavity 1178 of the acetabular shell 1170 when a surgeon is fitting the assembly 1110 into the acetabular shell 1170. In some embodiments, the metal ring 1140 may be shaped as a sleeve that encases the entire outer wall 1126 of the ceramic liner 1120.

Figure 12:
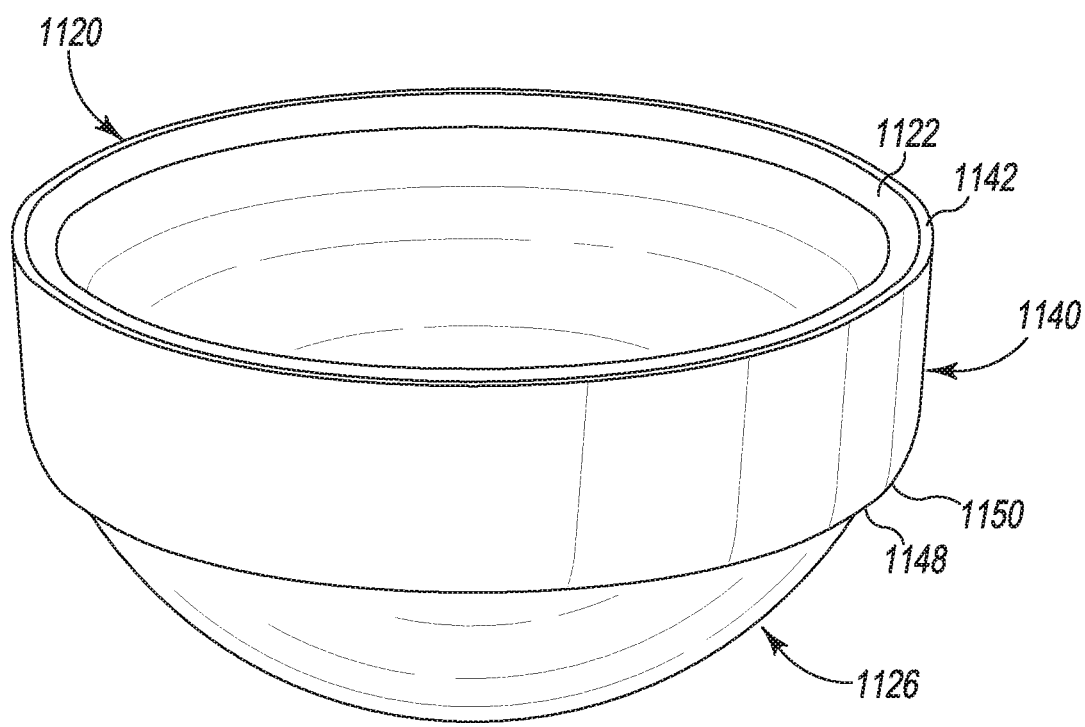
FIG. 12 is a perspective view of the ceramic acetabular shell liner of FIG. 11 with the metal ring affixed thereto.

Referring now to FIG. 12, a perspective view of the acetabular shell liner assembly 1110 in its assembled form is shown. As can be seen, the distal rim 1142 of the metal ring 1140 is substantially co-planar with the rim 1122 of the acetabular shell liner component 1120. The inner wall 1144 of the metal ring 1140 and the outer wall 1126 of the acetabular shell liner 1120 may be tapered to provide a press fit between the metal ring 1140 and the liner 1120, such that when the metal ring 1140 is slid onto the liner 1120 (e.g., in a distal direction), the metal ring 1140 is unable to slide farther (e.g., in the distal direction) once the rim 1122 and the distal rim 1142 are substantially co-planar. As shown in FIG. 12, the outer wall 1126 extends beyond the proximal rim 1148, in the proximal direction. However, in some embodiments and as stated above, the metal ring 1140 may encase the entire outer wall 1126 of the liner 1120.

Figure 13:
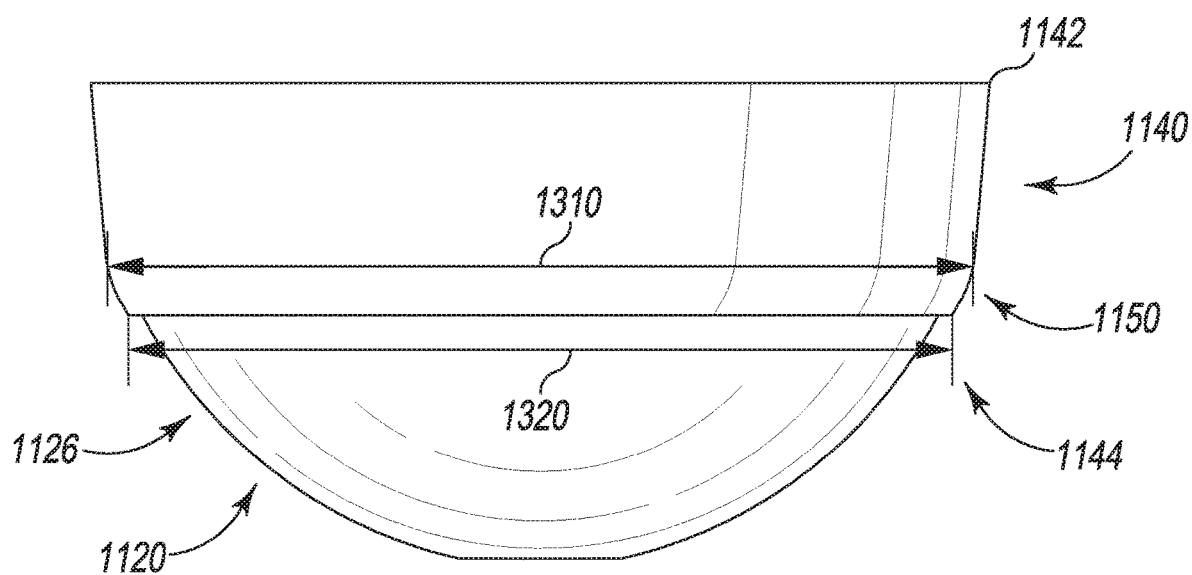
FIG. 13 is an elevation view of the ceramic acetabular shell liner of FIG. 11 with the metal ring affixed thereto.

Referring now to FIG. 13, from the elevation view, it can be seen that the lead-in surface 1150 is rounded to smoothly align the assembly 1110 into the cavity 1178 (e.g., into engagement with the inner wall 1174) of the shell 1170 when the assembly 1110 is inserted into the shell 1170 by a surgeon during a hip arthroplasty surgical procedure. As shown, the lead-in surface 1150 is somewhat conical in shape in that the metal ring 1140 has a diameter 1310 that is greater than another diameter 1320 closer to the proximal rim 1148 (e.g., the diameter of the metal ring 1140 gradually increases as a function of its distance from the proximal rim 1148).

Figure 14:
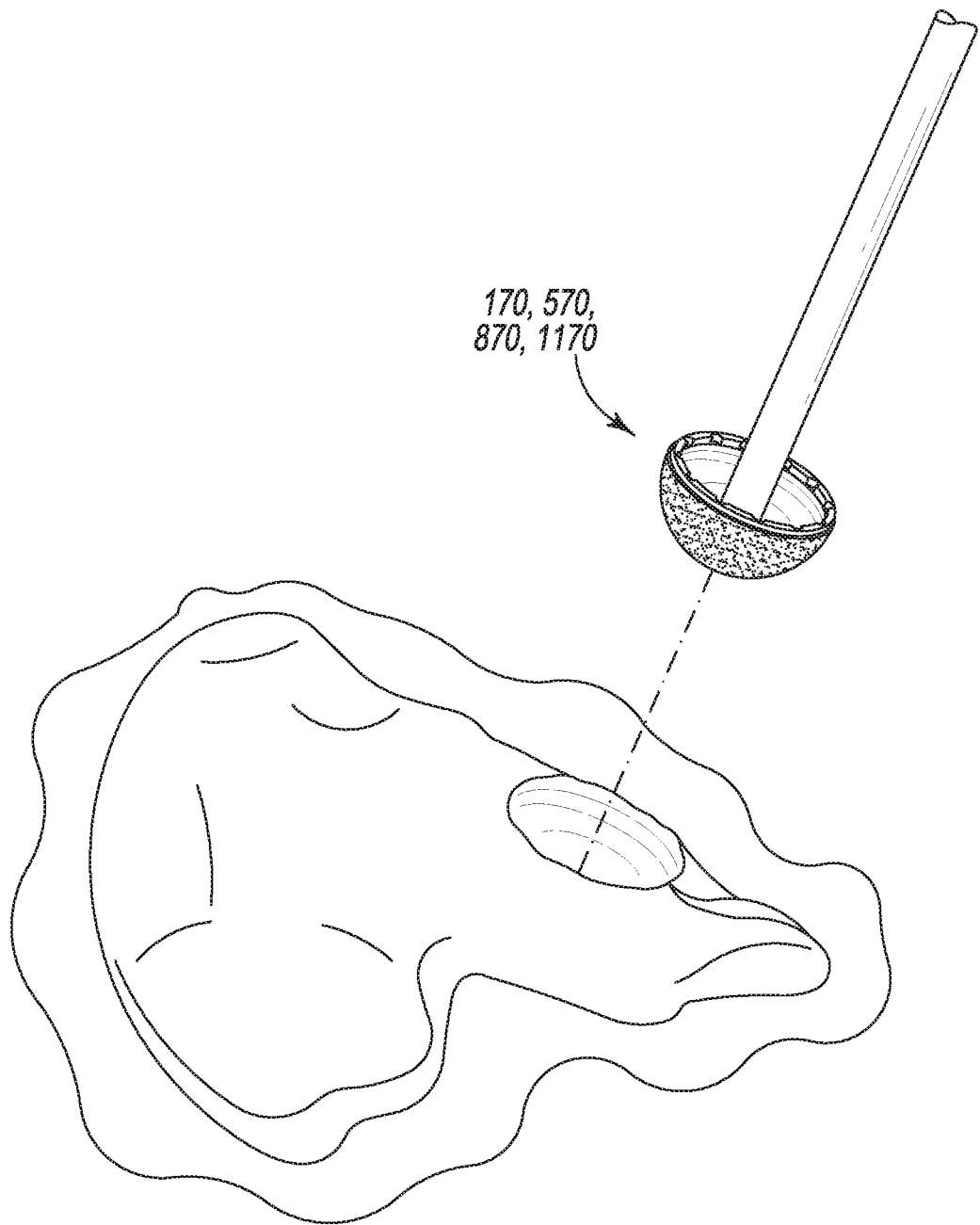
FIG. 14 is a perspective view of a patient's acetabulum with an acetabular shell being advanced towards the acetabulum.

Referring now to FIG. 14, a method for using a modular acetabular prosthesis (e.g., the prosthesis 100, 500, 800, 1100) in a hip arthroplasty procedure may begin with a surgeon inserting an acetabular shell (e.g., the shell 170, 570, 870, 1170) into a surgically prepared (e.g., by a surgical reamer) acetabulum of a patient. The surgeon may press fit the acetabular shell into place using a driver tool. In some embodiments, the surgeon may additionally thread one or more screws through one or more bores in the acetabular shell to further secure the shell in the acetabulum. In yet other embodiments, the surgeon may utilize other techniques, such as use of orthopaedic cement, to secure the shell into the acetabulum.

Figure 15:
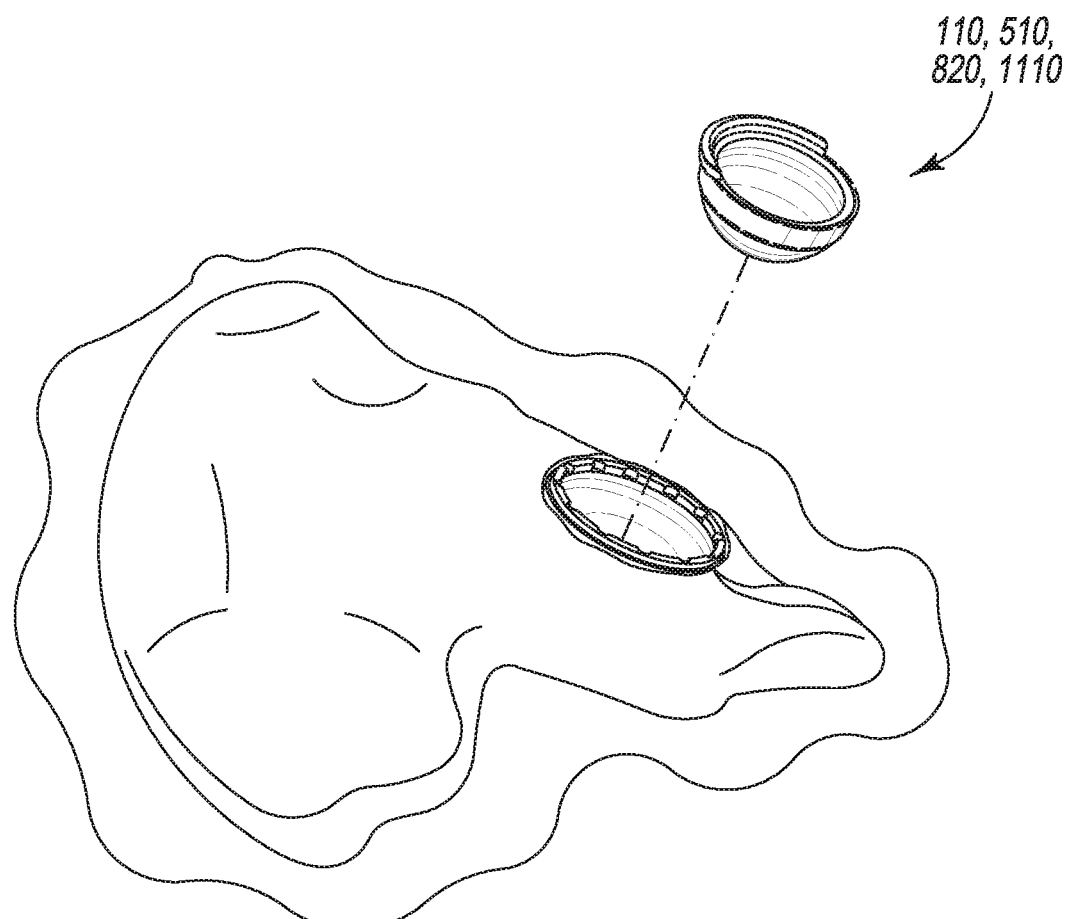
FIG. 15 is a perspective view of the patient's acetabulum with the acetabular shell inserted into the acetabulum and an acetabular shell liner being advanced towards the acetabular shell.

Referring now to FIG. 15, the surgeon may subsequently secure, into the acetabular shell (which has been inserted into the acetabulum, as described above), an acetabular shell liner assembly (e.g., the acetabular shell liner assembly 110, 510, 820, 1110). In the case of the acetabular shell liner assembly 1110, the lead-in surface 1150 of the metal ring 1140 aligns the assembly into the acetabular shell and absorbs any impacts with any portion of the acetabular shell (e.g., the inner wall) that may occur during the process. As described above, the acetabular shell liner may be shaped to lock into the acetabular shell (e.g., due to the tapered outer wall of the acetabular shell liner). Additionally or alternatively, in some embodiments, the acetabular shell liner may be secured into the acetabular shell using another mechanism (e.g., one or more screws).

Figure 16:
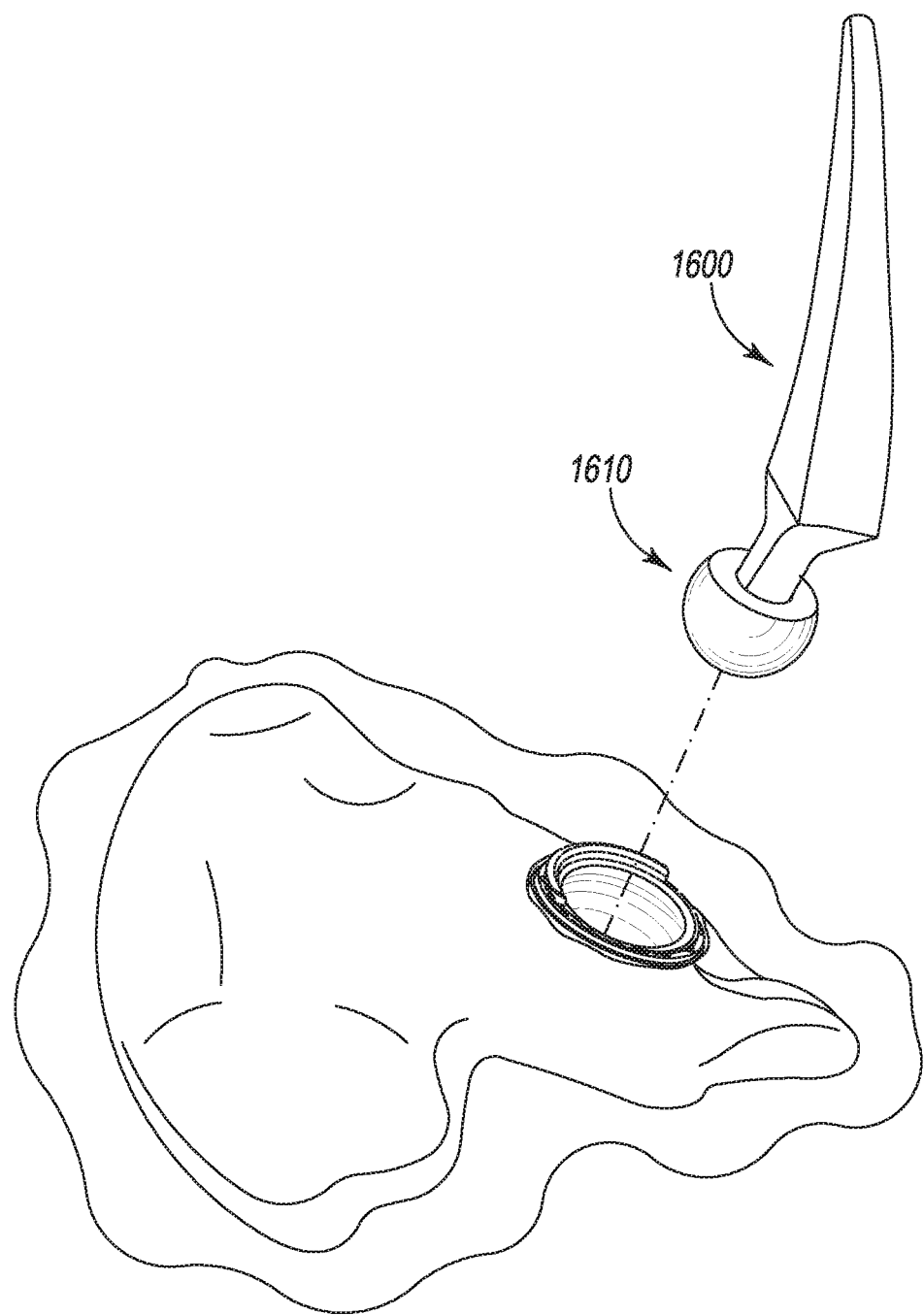
FIG. 16 is a perspective view of the patient's acetabulum with the acetabular shell and liner inserted and a femoral prosthesis component being advanced towards a cavity in the liner.
Figure 17:
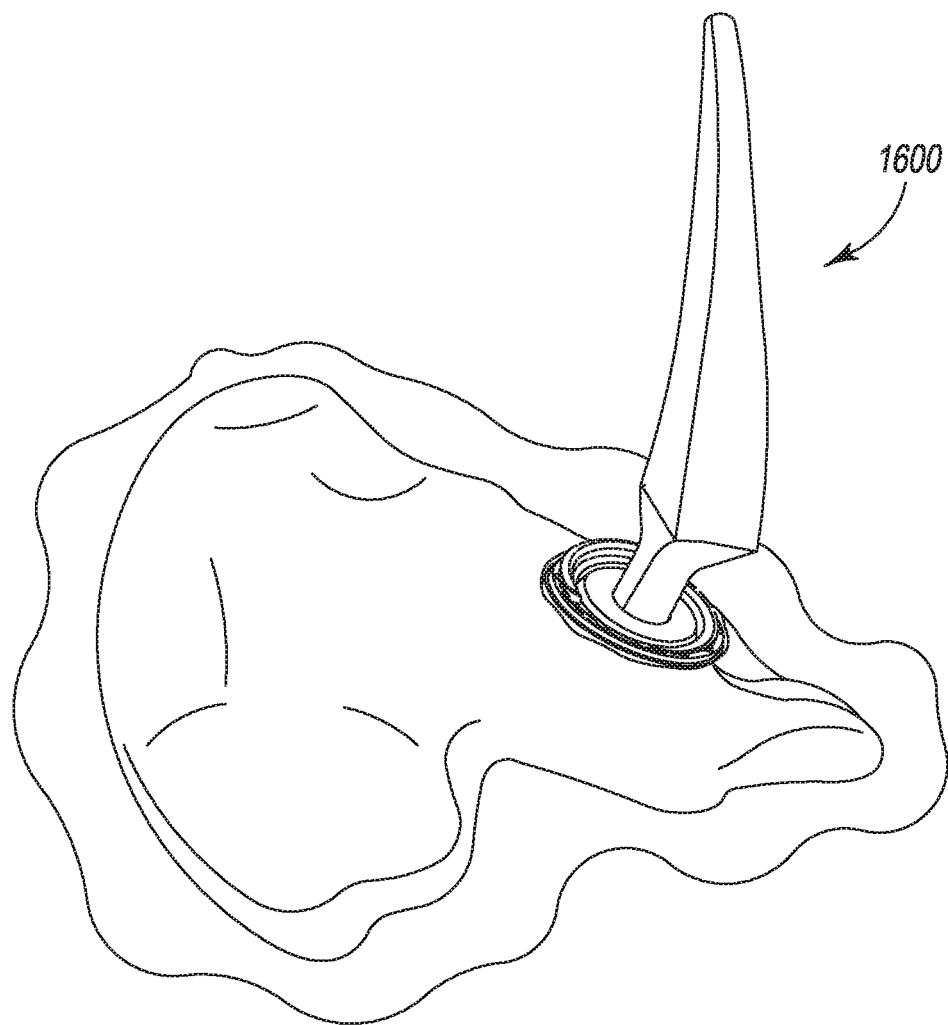
FIG. 17 is a perspective view of the femoral prosthesis fitted into the liner.

Referring now to FIGS. 16 and 17, with the acetabular shell and the acetabular shell liner assembly in the patient's acetabulum, the surgeon may fit a head of a femoral prosthesis into a cavity defined by the acetabular shell liner. In subsequent steps, the surgeon may test the fit and range of motion of the femoral head in the modular acetabular prosthesis. In some embodiments, the acetabular shell and/or liner assembly may be or include trial components (e.g., instruments) that the surgeon may swap out with other trial components having the features described herein, before determining that a particular combination of acetabular shell and liner assembly (e.g., which may include an augment) provides a satisfactory fit and range of motion. Afterwards, the surgeon may replace the trial components (e.g., instruments) with permanent implant versions of the components.

While certain illustrative embodiments have been described in detail in the drawings and the foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An acetabular prosthesis for use in a hip arthroplasty surgical procedure, the acetabular prosthesis comprising:
 a ceramic acetabular shell liner component configured to be secured to an acetabular shell component;
 a metal ring affixed to and encircling the ceramic acetabular shell liner component, wherein the metal ring includes a distal rim and a set of keys and wherein each key of the set of keys extends distally away from the distal rim and curves outwardly from the distal rim; and
 an augment molded over the set of keys and distally extending from the metal ring, wherein the augment is shaped to modify a range of motion of a femoral prosthetic component when the femoral prosthetic component is fitted into the ceramic acetabular shell liner component.

2. The acetabular prosthesis of claim 1, wherein the ceramic acetabular shell liner component is semi-hemispherical in shape and the augment causes the acetabular prosthesis to be over-hemispherical in shape.

3. The acetabular prosthesis of claim 1, wherein the ceramic acetabular shell liner component comprises an outer wall that is shaped to define a channel around a perimeter of the outer wall and the metal ring is secured within the channel.

4. The acetabular prosthesis of claim 3, wherein the metal ring comprises titanium.

5. The acetabular prosthesis of claim 3, wherein the metal ring is at least partially coated with a polymeric material.

6. The acetabular prosthesis of claim 3, wherein each key of the set of keys is formed from a polymeric material.

7. The acetabular prosthesis of claim 1, wherein the augment comprises a polymeric material.

8. An acetabular prosthesis for use in a hip arthroplasty surgical procedure, the acetabular prosthesis comprising:
 a ceramic acetabular shell liner component configured to be secured to an acetabular shell component;
 a metal ring affixed to and encircling the ceramic acetabular shell liner component, wherein the metal ring includes a distal rim and a set of keys that extend from the distal rim; and
 an augment molded over the set of keys and distally extending from the metal ring, wherein the augment is shaped to modify a range of motion of a femoral prosthetic component when the femoral prosthetic component is fitted into the ceramic acetabular shell liner component.

9. The acetabular prosthesis of claim 8, wherein the ceramic acetabular shell liner component is semi-hemispherical in shape and the augment causes the acetabular prosthesis to be over-hemispherical in shape.

10. The acetabular prosthesis of claim 8, wherein the ceramic acetabular shell liner component comprises an outer wall that is shaped to define a channel around a perimeter of the outer wall and the metal ring is secured within the channel.

11. The acetabular prosthesis of claim 8, wherein the metal ring comprises titanium.

12. The acetabular prosthesis of claim 8, wherein the metal ring is at least partially coated with a polymeric material.

13. The acetabular prosthesis of claim 8, wherein the augment comprises a polymeric material.

14. An acetabular prosthesis for use in a hip arthroplasty surgical procedure, the acetabular prosthesis comprising:
 a ceramic acetabular shell liner component configured to be secured to an acetabular shell component;
 a metal ring affixed to and encircling the ceramic acetabular shell liner component, wherein the metal ring includes a distal rim and a set of keys that extend away from the distal rim; and
 an augment molded over the set of keys of the metal ring, wherein the augment extends radially from a distal rim of the metal ring and is shaped to modify a range of motion of a femoral prosthetic component when the femoral prosthetic component is fitted into the ceramic acetabular shell liner component.

15. The acetabular prosthesis of claim 14, wherein the ceramic acetabular shell liner component is semi-hemispherical in shape and the augment causes the acetabular prosthesis to be over-hemispherical in shape.

16. The acetabular prosthesis of claim 14, wherein the ceramic acetabular shell liner component comprises an outer wall that is shaped to define a channel around a perimeter of the outer wall and the metal ring is secured within the channel.

17. The acetabular prosthesis of claim 14, wherein the metal ring comprises titanium.

18. The acetabular prosthesis of claim 14, wherein the metal ring is at least partially coated with a polymeric material.

19. The acetabular prosthesis of claim 14, wherein each key of the set of keys is formed from a polymeric material.

20. The acetabular prosthesis of claim 14, wherein the augment comprises a polymeric material.

* * * * *